United States Patent [19]

Miyahara et al.

[11] Patent Number: 5,106,301
[45] Date of Patent: Apr. 21, 1992

[54] METHOD FOR INSPECTING THE ROOT CANAL WITH A RADIOPAQUE IMPRESSION MATERIAL

[75] Inventors: Atsumu Miyahara, Higashiosaka; Hachiro Sasaki, Sapporo; Shunichi Futami, Nagareyama, all of Japan

[73] Assignee: G-C Dental Industrial Corp., Tokyo, Japan

[21] Appl. No.: 728,344

[22] Filed: Jul. 11, 1991

Related U.S. Application Data

[62] Division of Ser. No. 316,536, Feb. 27, 1989.

[30] Foreign Application Priority Data

Dec. 26, 1986 [JP] Japan .................................. 61-314806

[51] Int. Cl.⁵ .............................................. A61C 9/00
[52] U.S. Cl. ..................................... 433/214; 433/224
[58] Field of Search ...................... 433/214, 224, 81, 40

[56] References Cited

U.S. PATENT DOCUMENTS

| | | | |
|---|---|---|---|
| 3,925,895 | 12/1975 | Kliment et al. | 433/224 |
| 4,035,435 | 7/1977 | Hittmair et al. | 433/214 |
| 4,362,508 | 12/1982 | Soderstrom | 433/224 |
| 4,629,746 | 12/1986 | Michl et al. | 433/228.1 |

*Primary Examiner*—Cary E. O'Connor
*Attorney, Agent, or Firm*—Oblon, Spivak, McClelland, Maier & Neustadt

[57] ABSTRACT

A method for inspecting the root canal comprising using a room temperature-setting, rubbery and elastic impression material, typically a silicon impression material and 20.0 to 75.0% by weight of a radiopaque substance contained therein, which shows a solubility of 0.2 grams and less per 100 ml of water of 20° C. and is in the form of finely divided powders having a mean particle size of $5 \times 10^{-3} \sim 10$ micrometers.

26 Claims, No Drawings

METHOD FOR INSPECTING THE ROOT CANAL WITH A RADIOPAQUE IMPRESSION MATERIAL

This is a division of application Ser. No. 07/316,536, filed Feb. 27, 1989, now abandoned, which in turn is a continuation of application Ser. No. 07/127,382 filed, Dec. 2, 1987, now abandoned.

BACKGROUND OF THE INVENTION

1. Field of the Invention

The present invention relates to a radiopaque impression material for inspecting the root canal, which is used as the material to enable easy insepction and appreciation of the full-aspect of the rool canal for exact treatment, when performing endodontics for the preservation and retainment of teeth in odontotherapy.

2. Statement of the Prior Art

A natural tooth is of the structure comprising outside enamel and inside dentine, in which there is further the root canal having the dental pulp (nerves) therein. However precise a denture (a false tooth) may be to the wearer, it is in no way superior to a natural tooth. For that reason, endodontics to recover a natural tooth holds a vital position in dental therapy, and is a remedy as fundamental and important as periodontology.

For treating pulpal diseases such as endodontitis caused by pulpal caries or tooth devitalization caused by pulpal gangrene or necrosis, endodontics is performed to retain and make effective use of natural teeth as long as possible.

Endodontics is a remedy for the root canal, which has for its object to appropriately treat the interior of the root canal, the dental pulp of which is devitalized.

Such clinical treatment of the root canal involves the following three remedial processes.

1. Probing of the configuration, and measuring the size, of the root canal.
2. Preparation and cleaning of the root canal.
3. Root canal filling.

First of all, the state of the root canal, parodontium, etc. are appreciated by roentgenography to determine a remedial scheme. Following the remedial scheme, the dental pulp is removed with the use of a spiral bar called a broach. Afterwards, the interior of the root canal is cleaned to a completely aseptic condition to enlarge and prepare it, and is then usually filled with a gutta-percha point or a paste agent to fill it for complete sealing. In such endodontics, that is to say, the treatment of the root canal, roentgenography and roentgenological examination are now generally performed as the means effective to get hold of the complicated configuration of the root canal.

Prior to the enlargement and cleaning of the root canal, it is required to observe and consider the configuration and length of the root canal and the state of its lateral branches and accessory root canals in more detail. An X-ray photograph is a product of light and shadow made by roentgenopaque and roentgenoparent substances. Treatments are now performed by getting two-dimensional hold of a tooth or the root canal, each of a three-dimensional configuration, by the observation of an indistinct X-ray photograph and imaging the root canal of a three-dimensional configuration through high-degree knowledge and expertness. For such appropriate treatment of teeth, it is absolutely required to get accurate hold of the configuration, number and length of the root canal and the distribution of its lateral branches and accessory root canals.

Next, the root canal is cut and enlarged with the use of a reamer and K- and H-type files for polishing and cleaning. A gutta-percha point or a root canal filling material paste is filled as the root canal filling agent in the thus formed root canal void for complete sealing of the root canal and closing of the apical foramen. In this manner, the treatment of the root canal with endodontics is completed.

The object of the treatment of the root canal in endodontics is to fill the root canal and free it of any dead space by filling of a solid root canal filling material such as gutta-percha and silver points, or pasty root canal filling materials composed mainly of calcium hydroxide and zinc oxide eugenol. The requirements to this end are the proper preparation and complete cleaning of the root canal. For the proper preparation and complete cleaning of the root canal, it is required to get hold of the configuration, number and length of the root canal and the distribution of its lateral branches and accessory root canals by the observation of a plane X-ray photograph. However, it has been impossible to catch hold of the complicated state of the root canal even with recourse to high-degree expertness and experience. Further, the cubic figure of the root canal cannot direcly be appreciated, since an X-ray photograph is two-dimensional. Considerable difficulty has been encountered in the treatment of the root canal of such a complicated configuration, and makes it impossible to perform perfect root canal filling. This is responsible for recurrence of dental caries or periodontal diseases after the treatment.

Further, the X-ray photograph of teeth is now still of unclear roetgenopaqueness. The length of the root canal may be measured by the insertion of a file, etc. thereinto, but it is impossible to get hold of the width and configuration of root canal. Nonetheless, not until now is any roentgenopaque impression material effective for root canal examinations found. For exact endodontics, it is required to make direct or quasi-direct observation of the interior of the root canal before and after operation.

SUMMARY OF THE INVENTION

It has now been found that an impression material for the inspection of the root canal can be obtained by imparting roentgenopaque properties to a rubbery and elastic impression material for dental purposes, which can give a distinct roentgenogram of the complicated interior of the root canal and be poured into the details of the root canal so as to obtain a three-dimensional figure thereof. More specifically, the silicon impression material to which roentgenopaque properties are imparted is poured into the root canal of a tooth before and after operation to compare a roentgenogram with a cubic impression mould moulded from the root canal and get three-dimensional hold of the state of the root canal, whereby the root canal can be enlarged and cleaned. The impression material of the present invention is sufficiently helpful in determining whether or not the enlargement of the root canal is feasible, thereby allowing easy correction of the root canal, which has heretofore been unfeasible in the prior art.

DETAILED EXPLANATION OF THE INVENTION

The radiopaque substance acts as the filler, and may be used in place of, or together with, the conventional filler.

For the room temperature-setting, rubbery and elastic impression materials for dental purposes, use is made of condensation and addition polymerization type silicone impression materials as well as polysulfide and polyether impression materials. The polysulfide impression material is less susceptible to setting and shows relatively large elastic deformation. In the case of moulding (impression-taking) of a detail line such as the root canal, therefore, attention should be paid to the rate of removal of that impression material, since it is hard to reproduce the precise state of the root canal, partly because difficulty is involved in the removal of that material from within the root canal, and partly because that material is pulled and elongated.

Referring to the polyether impression material, since difficulty is experienced in pouring it into the root canal due to the absence of flowability, a certain pressure is needed. Further, care should be taken in using the polyether impression material as the radiopaque impression material for the insepction of the root canal, since it shows high water absorption and is cured into a hard body, which is easily torn off and causes a slight drop in the accuracy of a detail line mould such as a root canal mould. However, the silicone impression materials are optimum for the radiopaque impression material for the inspection of the root canal according to the present invention, since it excels in elasticity and hydrophobic nature and is harmless to the human body. The room temperature-setting, rubbery and elastic impression material for the inspection of the root canal usable in the present invention should preferably be based on the condensation and addition polymerization types. It is possible for the first time to take an X-ray photograph of the details of the root canal by imparting roentgenopaqueness to these two types of the dental silicone impression materials and filling them into the details of the root canal. After setting, the set body can easily be removed to obtain a cubic figure of the configuration of the root canal, etc., by means of which the enlargement and preparation of the root canal can easily be observed and ascertained.

The radiopaque materials used in the present invention act as the fillers, and may be used in place of, or together with, the conventional fillers, but should not be harmful and toxic to teeth and periodontium. Hence, any radiopaque substance having a solubility exceeding 0.2 grams per 100 ml of water of 20° C. must not be used, partly because teeth and periodontium are adversely affected by its dissolution, and partly because it hinders the setting reaction of the silicone impression material.

The radiopaque substance fit for the purpose of the present invention is limited to an inert substance showing a solubility of up to 0.2 grams per 100 ml of water of 20° C. Included in the substances which are of high roentgenopaque properties, show a solubility of up to 0.2 grams per 100 ml of water of 20° C. and are untoxic and harmless, are powders of metals such as zinc, ytterbium, yttrium, gadolinium, zirconium, strontium, tungusten, tantalum, niobium, molybdenum and lanthanum; finely divided powders of alloys of such metals; oxides such as yttrium oxide, bismuth oxide, ytterbium oxide, tungsten oxide, niobium oxide, tantalum oxide and molybdenum oxide; fluorides such as strontium fluoride, yttrium fluoride, bismuth fluoride, lanthanum fluoride and ytterbium fluoride; sulfates such as barium sulfate and strontium sulfate; carbonates such as bismuth oxycarbonate and strontium carbonate; tungstates such as calcium tungstate; and carbides such as tungsten carbide, molybdenum carbide, niobium carbide, tantalum carbide and zirconium carbide.

The concentration of the radiopaque substance should be such that the radiopaque impression material for the inspection of the root canal shows suitable flowability and roentgenopaque properties. In this connection, however, it should be noted that the flowability and roentgenopaque properties tend to be contrary to each other because of the radiopaque substance being in the form of finely divided powders, i.e., in the solid form. When the radiopaque substance is too small in quantity, no effective roentgenopaque properties are obtained. In particular, it is required that the radiopaque substance used in the present invention is distinctively distinguishable from enamel, and be readily pourable into the details of the root canal by means of a spiral tool called a lentulo. An excessive amount of the radiopaque substance is unfit for the purpose of the present invention, since difficulty is encountered in allowing it to flow into the details of the root canal.

Hence, when the radiopaque substance is used in an amount of less than 20.0% by weight with respect to the room temperature-setting silicone impression material, the boundary of the impression material poured into the root canal's void and the root canal's wall becomes so indistinct that it is especially difficult for the dentist to get hold of the complicated configuration and dimensions of the root canal and make exact inspection thereof. It is required, therefore, that, in order to obtain effective roentgenopaque properties, the radiopaque substance used in the present invention is added to the room temperature-setting silicone impression material in an amount of at least 20.0% by weight.

When the amount of the radiopaque substance with respect to the room temperature-setting silicone impression material exceeds 75.0% by weight, it is impossible to obtain any distinct roentgenogram of the details of the root canal, since that impression material loses its flowability, that is one function dispensible thereto, and does not flow into the details of the root canal. Moreover, because of the presence of too large an amount of the finely divided powders of the radiopaque substance, the silicone impression material loses its rubber elasticity to such an extreme degree that it becomes brittle and tends to be easily torn off, thus making it very difficult to remove the cured impression from within the root canal.

It is required, therefore, that the radiopaque substance be used in an amount of up to 75.0% by weight with respect to the room temperature-setting silicone impression material so as to permit it to flow into the details of the root canal. In other words, the concentration of the radiopaque substance enough to show effective roentgenopaque properties and flow into the details of the root canal should be limited to a range of 20.0% by weight to 75.0% by weight with respect to the room temperature-setting silicone impression material. More preferably, the concentration of the radiopaque substance sufficient to show excellent roentgenopaque properties, make a distinct figure of the root canal and render it possible to perform complete root canal treatment is in a range of 25.0% by weight to 70.0% by weight with respect to the room temperature-setting silicone impression material.

Further, the mean particle size of the finely divided radiopaque substance powders should be such that the flowability permitting the root canal-inspecting impression material to perform its own function and the effective roentgenopaque properties are assured. The finely divided radiopaque substance powders having a mean particle size of less than $5 \times 10^{-3}$ micrometer are unsuitable, since they give rise to a considerable decrease in the flowability of the impression material due to their large specific surface area, and their amount to be contained in the impression material is reduced to lower the roentgenopaque properties thereof. The finely divided radiopaque substance powders having a mean particle size exceeding 10 micrometers are also unsuitable, partly because it is impossible to pour the root canal-inspecting impression material containing them into the details of the root canal, and partly because when the root canal is moulded (for impression-taking) after setting, the moulded surface tends to roughen, thus making it impossible to obtain any fine cubic figure of the details of the root canal. Hence, the mean particle size of the radiopaque substance powders used with the root canal-inspecting impression material should be limited to $5 \times 10^{-3}$ to 10 micrometers. The shape of the finely divided radiopaque substance powders is preferably as close to a spherical shape having a reduced surface area as possible, since the amount thereof to be contained in the impression material is increased.

It is to be understood that these radiopaque substances may be used alone or in admixture, when incorporated into the room temperature-setting silicone impression material.

In general, the room temperature-setting, rubbery and elastic impression material for dental purposes is based on a pasty two-component system comprising a base and a catalyst and a three-component system comprising a pasty base-catalyst combination and a liquid reactor. According to the present invention, however, either one of these systems may be used, provided that the required quantity of one or two or more of the radiopaque substances showing a solubility of up to 0.2 grams per 100 ml of water of 20° C. is incorporated into the room temperature-setting, rubbery and elastic impression material for dental purposes. On the other hand, the room temperature-setting silicone impression materials for dental purposes usable in the present invention are known ones of the condensation and addition polymerization types comprising the following typical components.

A: Condensation Polymerization Type Silicone Impression Materials a) hydroxydimethylpolysiloxane having hydroxide groups on its both terminals b) ortho or polyethyl silicate having an ethoxy group as the crosslinker c) organometallic compounds such as dibutyltin acetate, dibutyltin laurate and lead octenate used as the condensation polymerization catalyst d) fillers such as diatomaceous earth and silica, and e) coloring material, perfumes, flowability regulators and plasticizers which may be used, if required.

B: Addition Polymerization Type Silicone Impression Materials a) vinylpolymethylsiloxane having a terminal vinyl group, b) hydrogenopolymethylsiloxane having active hydrogen groups on its both terminals, c) addition polymerization catalysts such as platinum base catalysts, d) fillers such as diatomaceous earth and silica, and e) coloring materials, perfumes, flowability regulators and plasticizers which may be used, if required.

EXAMPLES

The present invention will now be explained with reference to the following non-restrictive examples.

A: Condensation Polymerization Type Silicone Impression Materials for Inspecting the Root Canal

EXAMPLE 1

| Components I | |
| --- | --- |
| Hydroxydimethylpolysiloxane | 70 |
| Finely divided barium sulfate powders (having a mean particle size of 0.2 micrometers) | 30 |
| | 100 wt. % |

The components I were sufficiently mixed and kneaded together for 60 minutes in a mixer to prepare a base.

| Components II | |
| --- | --- |
| Vaseline | 20 |
| Dibutyltin laurate | 4 |
| Polyethyl silicate | 25 |
| Finely divided barium sulfate powders (having a mean particle size of 0.2 micrometers) | 50 |
| Red iron oxide | 1 |
| | 100 wt. % |

The components II were sufficiently mixed and kneaded together for 60 minutes in a mixer to prepare a catalyst.

The base and catalyst in a weight ratio of 2:1 were mixed on a mixing pad for 30 seconds by means of a spatula. The product was cured in four minutes.

EXAMPLE 2

| Components I | |
| --- | --- |
| Hydroxydimethylpolysiloxane | 60 |
| Finely divided tungsten oxide powder (having a mean particle size of 0.04 micrometers) | 40 |
| | 100 wt. % |

The components I were sufficiently mixed and kneaded together for 45 minutes in a mixer into a base.

| Components II | |
| --- | --- |
| Vaseline | 16 |
| Dibutyltin acetate | 4 |
| Finely divided strontium sulfate powders (having a mean particle size of 0.3 micrometers) | 55 |
| Polyethyl silicate | 24 |
| Red iron oxide | 1 |

| Components II | |
|---|---|
| | 100 wt. % |

The components II were sufficiently mixed and kneaded together for 30 minutes in a mixer into a catalyst.

The base and catalyst in a weight ratio of 2:1 were mixed on a mixing pad for 30 seconds by means of a spatula. The product was cured in 4.5 minutes.

EXAMPLE 3

| Components I | |
|---|---|
| Hydroxydimethylpolysiloxane | 50 |
| Finely divided zinc powders (having a mean particle size of 5.0 micrometers) | 50 |
| | 100 wt. % |

The components I were sufficiently mixed and kneaded together for 60 minutes in a mixer into a base.

| Components II | |
|---|---|
| Vaseline | 26.5 |
| Lead octoate | 28.0 |
| Finely divided bismuth oxycarbonate powders (having a mean particle size of 0.006 micrometers) | 35.0 |
| Finely divided niobium oxide powders (having a mean particle size of 0.4 micrometers) | 10.0 |
| Tinting red | 0.5 |
| | 100.0 wt. % |

The components II were sufficiently mixed and kneaded together for 45 minutes in a mixer into a catalyst.

| Components III | |
|---|---|
| Ethyl silicate | 50 |
| Silicone oil | 50 |
| | 100 wt. % |

The components III were sufficiently agitated and mixed together for 10 minutes in a mixer into a reactor.

The base, catalyst and reactor in a weight ratio of 5:2:1 were mixed together on a mixing pad for 40 seconds with the use of a spatula. The product was cured in 5 minutes.

COMPARATIVE EXAMPLE 1

| Components I | |
|---|---|
| Hydroxydimethylpolysiloxane | 70 |
| Silica (#300) | 30 |
| | 100 wt. % |

The components I were sufficiently mixed and kneaded together for 60 minutes in a mixer into a base.

| Components II | |
|---|---|
| Vaseline | 27.5 |
| Dibutyltin laurate | 29.0 |
| Polyethyl silicate | 23.0 |

| Components II | |
|---|---|
| Diatomaceous earth | 20.0 |
| Tinting red | 0.5 |
| | 100 wt. % |

The components II were sufficiently mixed and kneaded together for 40 minutes in a mixer into a catalyst.

The base and catalyst in a weight ratio of 5:2 were mixed together on a mixing pad for 40 seconds with the use of a spatula. The product was cured in 4.5 minutes.

The testing results of the impression materials A (Examples 1–3 and Comparative Example 1) are tabulated in Table 1 to be given later.

B: Addition Polymerization Type Silicone Impression Materials for Inspecting the Root Canal

EXAMPLE 4

| Component I | |
|---|---|
| Vinylpolymethylsiloxane | 38 |
| Hydrogenpolymethylsiloxane | 22 |
| Finely divided calcium tungstate powders (having a mean particle size of 0.01 micrometers) | 40 |
| | 100 wt. % |

The components I were sufficiently mixed and kneaded together for 60 minutes in a mixer into a base.

| Components II | |
|---|---|
| Vinylpolymethylsiloxane | 49.95 |
| Finely divided yttrium fluoride powders (having a mean particle size of 0.016 micrometers) | 25.0 |
| Finely divided tungsten carbide powders (having a mean particle size of 9.6 micrometers) | 25.0 |
| Hexachloroplatinic acid | 0.05 |

The components II were sufficiently mixed and kneaded together for 60 minutes in a mixer into a catalyst.

The base and catalyst in a weight ratio of 1:1 were mixed together on a mixing pad for 30 seconds with the use of a spatula. The product was cured in 4.5 minutes.

EXAMPLE 5

| Component I | |
|---|---|
| Vinylpolymethylsiloxane | 30 |
| Hydrogenpolymethylsiloxane | 20 |
| Finely divided lanthanum fluoride powders (having a mean particle size of 0.009 micrometers) | 10 |
| Finely divided strontium fluoride powders (having a mean particle size of 0.15 micrometers) | 40 |
| | 100 wt. % |

The components I were sufficiently mixed and kneaded together for 60 minutes in a mixer into a base.

| Composition II | |
|---|---|
| Vinylpolymethylsiloxane | 39.95 |
| Finely divided molybdenum oxide powders (having a mean particle size of 0.4 micrometers) | 20.0 |
| Finely divided bismuth fluoride powders (having | 40.0 |

-continued

| Composition II | |
|---|---|
| a mean particle size of 0.9 micrometers) | |
| Hexachloroplatinic acid | 0.05 |
| | 100 wt. % |

The components II were sufficiently mixed and kneaded together for 60 minutes into a catalyst.

The base and catalyst in a weight ratio of 1:1 were mixed together on a mixing pad for 30 seconds with the use of a spatula. The product was cured in 4.5 minutes.

EXAMPLE 6

| Components I | |
|---|---|
| Vinylpolymethylsiloxane | 27 |
| Hydrogenpolymethylsiloxane | 18 |
| Finely divided bismuth oxide powders (having a mean particle size of 8.5 micrometers) | 55 |
| | 100 wt. % |

The components I were sufficiently mixed and kneaded together for 60 minutes in a mixer into a base.

| Components II | |
|---|---|
| Vinylpolymethylsiloxane | 29.7 |
| Finely divided brass powders (having a mean particle size of 3.5 micrometers) | 70.0 |
| Hexachloroplatinic acid | 0.06 |
| Ultramarine | 0.24 |
| | 100.0 wt. % |

The components II were sufficiently mixed and kneaded together for 70 minutes in a mixer into a catalyst.

The base and catalyst in a weight ratio of 1:1 were mixed together on a mixing pad for 30 seconds by means of a spatula. The product was cured in 4 minutes.

EXAMPLE 7

| Components I | |
|---|---|
| Vinylpolymethylsiloxane | 50 |
| Hydrogenpolymethylsiloxane | 35 |
| Finely divided barium sulfate powders (having a mean particle size of 1.5 micrometers) | 15 |
| | 100 wt. % |

The components I were sufficiently mixed and kneaded together for 80 minutes in a mixer into a base.

| Components II | |
|---|---|
| Vinylpolymethylsiloxane | 74.6 |
| Finely divided yttrium oxide powders (having a mean particle size of 0.5 micrometers) | 10.0 |
| Finely divided calcium tungstate powders (having a mean particle size of 0.1 micrometer) | 15.0 |
| Hexachloroplatinic acid | 0.05 |
| Ultramarine | 0.35 |
| | 100.0 wt. % |

The components II were sufficiently mixed and kneaded together for 60 minutes in a mixer into a catalyst.

The base and catalyst in a weight ratio of 1:1 were mixed together on a mixing pad for 30 seconds with the use of a spatula. The product was cured in 5 minutes.

COMPARATIVE EXAMPLE 2

| Components I | |
|---|---|
| Vinylpolymethylsiloxane | 47 |
| Hydrogenpolymethylsiloxane | 28 |
| Silica (#300) | 25 |
| | 100 wt. % |

The components I were sufficiently mixed and kneaded together for 50 minutes in a mixer into a base.

| Components II | |
|---|---|
| Vinylpolymethylsiloxane | 84.95 |
| Silica (#300) | 15.0 |
| Hexachloroplatinic acid | 0.05 |
| | 100 wt. % |

The components II were sufficiently mixed and kneaded together for 50 minutes in a mixer into a catalyst.

The base and catalyst in a weight ratio of 1:1 were mixed together on a mixing pad for 30 seconds with the use of a spatula. The product was cured in 4.5 minutes.

The testing results of the impression materials B (Examples 4-7 and Comparative Example 2) are tabulated in Table 2 to be given later.

TABLE 1

Condensation Polymerization Type Silicone Impression Materials A for Inspecting the Root Canal

| Sample | Example 1 | Example 2 | Example 3 | Comparative Example 1 |
|---|---|---|---|---|
| Setting Time | 4 min. | 4.5 min. | 5 min. | 4.5 min. |
| Roentgenopaqueness according to ISO Standard | 3.5 | 4.5 | 4.0 | 0.5 and less |
| Roentgenopaqueness in Extracted Tooth | ⊚ | ⊚ | ⊚ | X |

⊚ : Distinct details of the root canal with the distinction higher than that of the roentgenopaqueness of enamel.
X: Extremely indistinct details of the root canal with no roentgenopaqueness.

TABLE 2

Addition Polymerization Type Silicone Impression Materials B for Inspecting the Root Canal

| Sample | Example 4 | Example 5 | Example 6 | Example 7 | Comparative Example 2 |
|---|---|---|---|---|---|
| Setting Time | 4.5 min. | 4.5 min. | 4 min. | 5 min. | 4.5 min. |
| Roentgenopaqueness according to ISO | 4.5 | 3.0 | 4.0 | 3.5 | 0.5 and less |

TABLE 2-continued

| | Addition Polymerization Type Silicone Impression Materials B for Inspecting the Root Canal | | | | |
|---|---|---|---|---|---|
| Sample | Example 4 | Example 5 | Example 6 | Example 7 | Comparative Example 2 |
| Standard Roentgenopaqueness in Extracted Tooth | ⊚ | ○ | ⊚ | ⊚ | X |

⊚ : Distinct details of the root canal with the distinction higher than that of the roentgenopaqueness of enamel.
○ : Nearly distinct details of the root canal with the distinction equal to or higher than that of the roentgenopaqueness of enamel.
X: Extremely indistinct details of the root canal with no roentgenopaqueness.

Measurement of Setting Time

A sample was placed in a stainless steel ring of 8.0 mm in height, 24.0 mm in inner diameter and 1.0 mm in thickness in a constant temperature room of a temperature of 23°±2° C. and a humidity of 50±10%. A 150 gram-Vicat needle (diameter 3.0 mm) was then stuck into the sample. The setting time is expressed in terms of the length of time from the commencement of mixing to the time at which the needle could not be stuck into the sample to a depth of up to 1.0 mm and less.

Measurement of Roentgenopaqueness with Standard Plate Provided by ISO

According to the method stipulated by ISO 4049, standard aluminium plates of 0.5 mm, 1.0 mm, 1.5 mm, 2.0 mm, 2.5 mm, 3.0 mm, 3.5 mm, 4.0 mm, 4.5 mm and 5.0 mm in thickness and a sample plates of 1.0 mm in thickness was X-rayed to determine which of the standard aluminium plates corresponds in thickness to the sample by comparison. The roentgenopaqueness of the sample is expressed in terms of the standard aluminium plate showing the same roentgenopaque properties.

EXAMPLE

The roentgenopaqueness of a sample of 1.0 mm in thickness is determined to be 2.0 mm, when it shows the same roentgenopaqueness as that of the standard aluminium plate of 2.0 mm in thickness.

The higher the figure, the stronger the roentgenopaquness.

Determination of Roentgenopaqueness in Teeth

A sample was poured into the root canal of the upper central incisor tooth of an extracted tooth with the use of a syringe or lentulo, and was cured with the insertion of a bar such as a gutta-percha point or file. Ten minutes after setting, the sample was roentgenized according to the method stipulated by ISO 4049 to observe the distinction of roentgenopaqueness.

⊚: Distinct details of the root canal with the distinction higher than that of the roentgenopaqueness of enamel.
○: Nearly distinct details of the root canal with the distinction equal to or higher than that of the roentgenopaqueness of enamel.
△: Indistinct details of the root canal with the distinction lower than that of the roentgenopaqueness of enamel.
X: Extremely indistinct details of the root canal with no roentgenopaqueness.

As clearly understood from the testing results given in Tables 1 and 2, the radiopaque impression materials for the inspection of the root canal, to which the radiopaque substances of the present invention are added, give more distinct roentgenograms and makes the discrimination of the root canal easier, as compared with the room temperature-setting, rubbery and elastic impression materials (Comparative Examples 1 and 2). Further, the impression of the details of the root canal can be taken without losing the properties of the dental rubbery and elastic impression materials.

EFFECT OF THE INVENTION

1. The content is cleared of the root canal prior to operation, and the rubbery impression material containing the radiopaque substance is poured thereinto by means of a spiral tool called a lentulo for setting. Thereafter, the impression material can be removed from within to consider the specific scheme or procedure for the enlargement of the root canal.
   The structure of a pulp chamber and the position, configuration and number of the orifice of the root canal may be observed as well.
2. After the completion of preparation of the root canal following its treatment, the root canal can be observed as it is. If insufficient, the root canal can be re-treated to insure proper treatment.
3. The preparation of the root canal can be ascertained.
   Perforation, bleeding and stricture of the root canal, a fractured root canal instrument and the positions of lateral branches of the root canal and accessory root canals may be observed and ascertained as well.

In endodontics, the insepction of the root canal has been performed relying upon intuition, experience and expertness. According to the present invention, however, such a radiopaque impression material for inspecting the root canal, which excels in roentgenopaque properties, is transported into the root canal by means of a syringe or lentulo, and a bar of suitable size such as a gutta-percha point or file is inserted into the root canal to the vicinity of its root apex. After setting of that impression material, roentgenography can be applied to inspect the configuration, number and length of the root canal. In addition, the details of the interior of the root canal can be observed by pulling that impression material from within. Thus, the present invention makes it possible for the first time to perform appropriate diagnosis and treatment activities.

What is claimed is:

1. A method for inspecting the root canal, which comprises the steps of:
   1. determining the configuration, size and length of the root canal and of its lateral and accessory branches by filling them with a room temperature setting, rubbery and elastic impression material containing 20.0 to 75.0% by weight of a radiopaque substance, 2. removing said impression material,
3. enlarging and cleaning the root canal and its lateral and accessory branches as necessary, and
4. filling the root canal and its lateral and accessory branches with a root canal filling material.

2. The method as defined in claim 1, wherein said room temperature-setting, rubbery and elastic impression material is a silicone impression material.

3. The method as defined in claim 1 or 2, wherein said radiopaque substance has a solubility of 0.2 g and less per 100 ml of water of 20° C., and is selected from the group consisting of powders of metals zinc, ytteribium, ittrium, gadolinium, zirconium, strontium, tungsten, tantalum, niobium, barium, bismuth, molybdenum and lanthanum, powders of alloys thereof, oxides, fluorides, sulfates, carbonates, tungstates and carbides thereof.

4. The method as defined in claim 1 or 2, wherein said radiopaque substance is finely divided powders expressed in terms of a mean particle size of $5 \times 10^{-3} \sim 10$ micrometers.

5. The method according to claim 2, wherein the silicone impression material is a condensation polymerization material.

6. The material according to claim 2, wherein the silicone impression material is an addition polymerization material.

7. The method according to claims 1 or 2, wherein the radiopaque substance has a solubility of 0.2 g and less per 100 ml of water at 20° C. and being a finely divided powder having a mean particle size of $5 \times 10^{-3} \sim 10$ micrometers.

8. The method according to claims 1 or 2, wherein said radiopaque substance is selected from the group consisting of powders of metals ytterbium, itrium, gadolinium, zirconium, strontium, tungsten, tantalum, niobium, bismuth, molybdenum and lanthanum, powders of alloys thereof, oxides, fluorides, sulfates, carbonates, tungstates and carbides thereof.

9. The method according to claim 8, wherein said radiopaque substance is a powder of ytterbium.

10. The method according to claim 8, wherein said radiopaque substance is a powder of itrium.

11. The method according to claim 8, wherein said radiopaque substance is a powder of gadolinium.

12. The method according to claim 8, wherein said radiopaque substance is a powder of zirconium.

13. The method according to claim 8, wherein said radiopaque substance is a powder of strontium.

14. The method according to claim 8, wherein said radiopaque substance is a powder of tungsten.

15. The method according to claim 8, wherein said radiopaque substance is a powder of tantalum.

16. The method according to claim 8, wherein said radiopaque substance is a powder of niobium.

17. The method according to claim 8, wherein said radiopaque substance is a powder of bismuth.

18. The method according to claim 8, wherein said radiopaque substance is a powder of molybdenum.

19. The method according to claim 8, wherein said radiopaque substance is a powder of lanthanum.

20. The method according to claim 8, wherein said radiopaque substance is a powder of alloys of said metals.

21. The method according to claim 8, wherein said radiopaque substance is a powder of an oxide of said metals.

22. The method according to claim 8, wherein said radiopaque substance is a powder of fluoride of said metals.

23. The method according to claim 8, wherein said radiopaque substance is a powder of a sulfate of said metals.

24. The method according to claim 8, wherein said radiopaque substance is a powder of a carbonate of said metals.

25. The method according to claim 8, wherein said radiopaque substance is a powder of a tungstate of said metals.

26. The method according to claim 8, wherein said radiopaque substance is a powder of a carbide of said metals.

* * * * *

UNITED STATES PATENT AND TRADEMARK OFFICE
CERTIFICATE OF CORRECTION

PATENT NO.   :   5,106,301
DATED        :   April 21, 1992
INVENTOR(S)  :   Atsumu Miyahara et al.

It is certified that error appears in the above-identified patent and that said Letters Patent is hereby corrected as shown below:

On the title page: Item [63]

The Related U.S. Application Data is incomplete, should be,

--Division of Ser. No. 316,536, Feb. 27, 1989, abandoned, which is a Continuation of Ser. No. 127,382, Dec. 2, 1987, abandoned--.

Signed and Sealed this

Thirteenth Day of July, 1993

Attest:

MICHAEL K. KIRK

*Attesting Officer*   Acting Commissioner of Patents and Trademarks